United States Patent [19]
Zech et al.

[11] Patent Number: 5,750,589
[45] Date of Patent: May 12, 1998

[54] HYDROPHILATED DENTAL IMPRESSION COMPOUNDS

[75] Inventors: Joachim Zech, Hechendorf; Erich Wanek, Kaufering; Günther Lechner, Wörthsee; Peter Bissinger, Köngisbrunn, all of Germany

[73] Assignee: Thera Patent GmbH & Co. KG Gesellschaft fur. Seefeld, Germany

[21] Appl. No.: 646,272

[22] PCT Filed: Sep. 15, 1995

[86] PCT No.: PCT/EP95/03638

§ 371 Date: May 16, 1996

§ 102(e) Date: May 16, 1996

[87] PCT Pub. No.: WO96/08230

PCT Pub. Date: Mar. 21, 1996

[30] Foreign Application Priority Data

Sep. 16, 1994 [DE] Germany ............. 44 33 139.8

[51] Int. Cl.$^6$ ............. A61K 6/10; C07F 7/08
[52] U.S. Cl. ............. 523/109; 523/120; 524/377; 524/588; 528/28; 528/29; 528/32; 433/214; 556/465
[58] Field of Search ............. 523/109, 120; 524/377, 588; 433/214; 556/465; 528/29, 32, 28

[56] References Cited

U.S. PATENT DOCUMENTS

| | | | |
|---|---|---|---|
| 4,248,750 | 2/1981 | Murakami et al. | 528/31 |
| 4,565,714 | 1/1986 | Koshar | 528/31 |
| 4,879,339 | 11/1989 | Yoshino et al. | 524/740 |
| 5,051,463 | 9/1991 | Yukimoto et al. | 524/377 |
| 5,138,009 | 8/1992 | Inoue | 528/15 |
| 5,367,001 | 11/1994 | Itoh et al. | 523/109 |
| 5,430,166 | 7/1995 | Klein et al. | 556/465 |

FOREIGN PATENT DOCUMENTS

| | | | |
|---|---|---|---|
| 3741575 | 12/1987 | Germany. | |
| 4010281 | 3/1990 | Germany. | |
| 4019249 | 6/1990 | Germany. | |
| 4207024 | 3/1993 | Germany. | |
| 2115020 | 5/1987 | Japan | 528/29 |

*Primary Examiner*—Andrew E. C. Merriam
*Attorney, Agent, or Firm*—Birch, Stewart, Kolasch & Birch, LLP

[57] ABSTRACT

The present invention relates to dental impression compounds which contain as hydrophilation agent 0.1 to 10 wt.-%, relative to the total weight of the compound, of a polyether carbosilane.

8 Claims, No Drawings

HYDROPHILATED DENTAL IMPRESSION COMPOUNDS

The present invention relates to dental impression compounds hydrophilated by special additives.

With dental impression compounds based on addition-crosslinking or condensation-crosslinking silicones or else based on polyether silicones and polyethers, there is the problem that the drawing sharpness of the impression is not satisfactory because of poor flow behaviour of the paste as a result of inadequate hydrophilia. This problem is described e.g. in DE-A-38 38 587, page 2, lines 19–23 or in EP-A-0 480 238, page 2, lines 1–26.

Very varied additives which increase the hydrophilia of the impression compounds have been described in the literature for the solution of this problem. A survey of the state of the art is found for example in EP-A-0 480 238, page 2, lines 20–38. Polyether siloxanes, such as are described for example in international application WO 87/03001 or in EP-B-0 231 420, have proved to be particularly effective additives.

All the additives admittedly show an improvement in the hydrophilia of the impression compounds; however, they also display a series of problems, which are listed in the following:

Increased water absorption, with the consequence of dimensional instability caused by swelling (DE-A-43 06 997, page 2, lines 44 et seq.).

Development of gas bubbles in the case of silicone impression compounds (EP-A-0 480 238, page 2, lines 27–38, and DE-A-43 06 997, page 2, lines 44–56).

Poor stability (EP-B-0 231 420, page 5, lines 13–27).

Delay in setting (DE-A-43 06 997, page 2, lines 53 et seq.)

Loss of hydrophilia after disinfection (DE-A-43 06 997, page 2, lines 37 et seq; also Journal of Prosthodontics, Volume 3, No. 1, 1994, pages 31–34).

Poor stability of polyether siloxanes vis-à-vis hydrolysis (DE-C-43 20 920, page 2, lines 32–36). The long-term effect of the hydrophilation over the service life of a moulding compound is thus not guaranteed with certainty.

The polyether siloxanes mentioned above which are particularly suitable for the hydrophilation of dental impression compounds do however have a major drawback. The dental impression compounds hydrophilated with them are not adequately stable vis-à-vis disinfection baths. The impressions produced during treatment are disinfected at least twice in the usual way and there is thus an unwanted loss of hydrophilia.

It is the object of the invention to make available hydrophilated dental impression compounds from which dental impressions with improved resistance to disinfection baths can be produced.

This object is achieved by dental impression compounds which contain 0.1 to 10 wt.-%, relative to the total weight of the compound, of a polyether carbosilane as hydrophilation agent.

Particularly preferred as hydrophilation agents are polyether carbosilanes of the following general formula $$Q-P-(OC_nH_{2n})_x-OT \qquad (I)$$

in which:

Q stands for $R_3Si-$ or

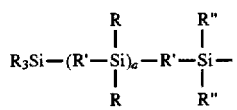

where every R in the molecule can be the same or different and stands for an aliphatic $C_1-C_{18}$, a cycloaliphatic $C_6-C_{12}$ or an aromatic $C_6-C_{12}$ hydrocarbon radical, which can optionally be substituted by halogen atoms, R' is a $C_1-C_{14}$ alkylene group, R" is R in the case of a≠0 or is R or $R_3SiR'$ in the case of a=0, and a=0–2;

P stands for a $C_2-C_{18}$ alkylene group, preferably a $C_2-C_{14}$ alkylene group or A—R'", where A represents a $C_2-C_{18}$ alkylene group and R'" a functional group from the following list:

$-NHC(O)-$, $-NHC(O)(CH_2)_{n-1}-$, $-NHC(O)C(O)-$, $-NHC(O)(CH_2)_vC(O)-$, $-OC(O)-$, $-OC(O)(CH_2)_{n-1}-$, $-OC(O)C(O)-$, $-OC(O)(CH_2)_vC(O)-$, $-OCH_2CH(OH)CH_2OC(O)(CH_2)_{n-1}-$, $-OCH_2CH(OH)CH_2OC(O)(CH_2)_vC(O)$ with v=1–12;

T is the same as H or stands for a $C_1-C_4$ alkyl radical or a $C_1-C_4$ acyl radical;

x stands for a number from 1 to 200, and n stands for an average number from 1 to 6, preferably 1 to 4.

The polyether part can be a homopolymer, but can also be a statistical, alternating or block copolymer.

Polyether carbosilanes of the following general formula are also particularly preferred as hydrophilation agents:

$$Q'-(P-(OC_nH_{2n})_x-OT)_2 \qquad (II)$$

in which:

Q' stands for $-SiR_2-X-SiR_2-$;

X stands for a divalent hydrocarbon radical, i.e. a $C_1-C_{18}$ alkylene, $C_6-C_{20}$ arylene, $C_5-C_{15}$ cycloalkylene and $C_5-C_{15}$ polycycloalkylene radical, which can optionally bear oxygen-containing groups, and where all other symbols have the same meaning as in the general formula (I).

Polyether carbosilanes of the following general formula are also particularly preferred as hydrophilation agents:

$$Q-P-(OC_nH_{2n})_x-OP-Q \qquad (III)$$

in which all symbols have the same meaning as in the general formula (I).

Polyether carbosilanes of the following general formula are also particularly preferred as hydrophilation agents:

$$Q-P'-(OC_nH_{2n})_x-OT \qquad (IV)$$

in which

P' stands for

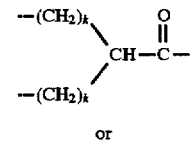

or

-continued

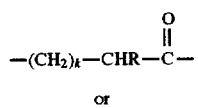

or

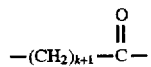

where k is 1–8; and
all other symbols have the same meaning as in the general formula (I).

Finally, polyether carbosilanes of the following general formula are particularly preferred as hydrophilation agents:

$$Q''(-P-(OC_nH_{2n})_xOT)_{o'}. \quad (V)$$

in which:

Q" stands for an oligomeric or polymeric carbosilane, where at least one silicon atom, but preferably 20–70% of the silicon atoms, are substituted by the radical —P—$(OC_nH_{2n})_xOT$) and thus o' is >1; and
all other symbols have the same meaning as in the general formula (I).

As already mentioned, impressions produced from conventional dental impression compounds do not display adequate stability vis-à-vis disinfection baths. As a result of the disinfection of the impressions, which takes place at least twice as a rule, a loss of hydrophilia occurs, which becomes noticeable in a poor flow behaviour of the aqueous plaster suspension when the impressions are cast. The determination of the edge angle can be used as a measure of the flow behaviour. The loss of hydrophilia is accompanied by an increasing edge angle. The edge angle is the angle which the edge of a water drop forms relative to the substrate surface (Walter Noll, Chemistry and Technology of Silicone, Academic Press, 1968, in particular pages 447 to 452). The hydrophilation agent according to the invention should be present in the dental impression compound in a sufficient quantity for the 10-second edge angle to be <55°, preferably <45°.

The decrease in the hydrophilia of silicone compounds hydrophilated for example with polyether siloxanes is presumably to be attributed to the fact that the hydrophilation agent is dissolved out in the disinfection bath.

The hydrophilation of silicone compounds with polyether siloxanes is described in the international application WO 87/03001 already mentioned above and EP-B-0 231 420. A suitable polyether siloxane has the following formula for example

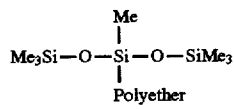

In the case of these compounds, the —Si—O— chain effects the compatibility with the silicone impression compounds, while the polyether portion is responsible for the hydrophilation and thus for the good flowability of the compound. One of the polyether carbosilanes suitable according to the invention has the following formula for example

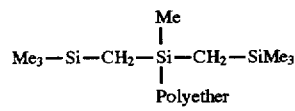

Because of the structure of the polyether carbosilanes, it was to be expected that their compatibility with the silicone compounds is poorer, because of the absence of the oxygen bridges, than is the case with the polyether siloxanes. It was therefore necessary to assume that the polyether carbosilanes to be used according to the invention can be dissolved out much more readily in the disinfection baths than can the known polyether siloxanes, and an even more pronounced loss of hydrophilia therefore had to be expected when the impressions were disinfected. Surprisingly, however, this is not the case. It was shown that the impressions produced from the dental impression compounds hydrophilated with the polyether carbosilanes according to the invention behave much more favourably as regards the maintenance of hydrophilia than do impressions which have been produced using silicone compounds hydrophilated with polyether siloxanes.

The dental impression compounds according to the invention also have the advantage that they are stable. It is stated in EP-B-0 231 420 on page 5 in lines 17–27 that the stability of hydrophilated silicones is poor because of moisture. A filler which absorbs or adsorbs water must thus be introduced into the compound in order to guarantee the stability of the hydrophilic silicone. This is not necessary with the dental impression compounds hydrophilated according to the invention. They are stable even without the addition of such fillers.

It is further of advantage that the plaster models produced with the dental impression compounds according to the invention have smooth surfaces. The state of the art (e.g. EP-B-0 268 347, page 2, lines 7–41 or DE-C-29 26 405, page 2, line 46 to page 3, line 10 or DE-A-43 06 997, page 2, lines 44–56) states that in the case of addition-crosslinked silicones there is the problem of the formation of gas bubbles, as a result of which the plaster model which is obtained by casting the hardened impression receives an unwanted spongy surface. In order to avoid this, finely dispersed platinum or palladium must be added as a hydrogen absorber. With the dental impression compounds according to the invention, this is not necessary. A plaster model which has been produced by casting an impression from a dental impression material according to the invention has a smooth surface even in the absence of hydrogen absorbers.

The basis of the dental impression compositions according to the invention is formed by known addition-crosslinking or condensation-crosslinking silicones, polyether silicones or polyethers. These materials have been described at length in the state of the art, so there is no need to discuss them in more detail here. Addition- or condensation-crosslinking silicones are described for example in U.S. Pat. No. 3,897,376, in EP-B-0 231 420 and also in U.S. Pat. No. 4,035,453 that is mentioned there on page 2, and in EP-A-0 480 238 (see in particular page 2, lines 3–26) and in EP-B-0 268 347. The disclosure of these patent specifications is also to be included here by reference. Polyether silicones are described inter alia for example in DE-A-37 41 575 and in DE-A-38 38 587, the disclosure of which is likewise also to be included here. Finally, polyethers are disclosed inter alia in DE-B-17 45 810 and in DE-A-43 06 997, the disclosure of which is likewise also to be included here.

As already mentioned above, the dental moulding materials according to the invention contain 0.1 to 10 wt.-%, relative to the total weight of the compound, of the polyether carbosilane as hydrophilation agent. The compounds preferably contain 0.5 to 5 wt.-% and in particular 1 to 4 wt.-% of the polyether carbosilane.

In the general formula (I) given above, R preferably stands for an aliphatic $C_1$–$C_6$ hydrocarbon radical, in particular a methyl or ethyl radical, a cycloaliphatic $C_6$–$C_8$ hydrocarbon radical or an aromatic $C_6$–$C_8$ hydrocarbon radical, in particular a phenyl radical.

R' preferably stands for a $C_1$–$C_6$ alkylene radical and in particular for a methylene or ethylene radical.

If P is not the same as A—R''', then P is preferably a $C_2$–$C_8$, in particular a $C_2$–$C_6$ alkylene group. If P is the same as A—R''', then S is preferably a $C_2$–$C_8$, in particular a $C_2$–$C_6$ alkylene group and R''' an O—C(=O) or NH—C(=O) group.

T preferably stands for H, for a methyl or ethyl radical or for an acetyl radical.

a is preferably 0, x preferably stands for a number from 1 to 50 and n preferably has a value of 2 to 2.5.

Particularly preferred polyether carbosilanes are the compounds listed in the following $Et_3Si-(CH_2)_3-O-(C_2H_4O)_y-CH_3$ $Et_3Si-CH_2-CH_2-O-(C_2H_4O)_y-CH_3$

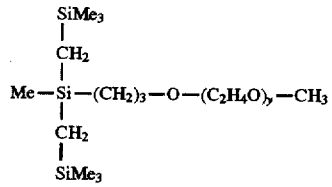

$(Me_3Si-CH_2)_3Si-(CH_2)_3-O-(C_2H_4O)_y-CH_3$ $Me_3Si-CH_2-SiMe_2-(CH_2)_3-O-(C_2H_4O)_y-CH_3$ $Me_3Si-(CH_2)_3-O-(C_2H_4O)_y-CH_3$ $Me_3Si-CH_2-CH_2-O-(C_2H_4O)_y-CH_3$ $Ph_3Si-(CH_2)_3-O-(C_2H_4O)_y-CH_3$, Ph=phenyl $Ph_3Si-CH_2-CH_2-O-(C_2H_4O)_y-CH_3$, Ph=phenyl $Cy_3Si-(CH_2)_3-O-(C_2H_4O)_y-CH_3$, Cy=cyclohexyl $Cy_3Si-CH_2-CH_2-O-(C_2H_4O)_y-CH_3$, Cy=cyclohexyl $(C_6H_{13})_3Si-(CH_2)_3-O-(C_2H_4O)_y-CH_3$ $(C_6H_{13})_3Si-CH_2-CH_2-O-(C_2H_4O)_y-CH_3$ in which y conforms to the relation:

$1 \leq y \leq 20$ or preferably $1 \leq y \leq 10$.

These compounds are described in DE-C-43 20 920 and GB-A-15 20 421 respectively as regards their structure and production. EP-A-0 367 381 describes similar compounds of an ionic nature. The disclosure of the named patent specifications is also to be included here by reference.

The named patent literature describes the use of such polyether carbosilanes with hydrophilic groups as surfactants in the aqueous medium or as foam-controlling agents. No reference of any kind to their use as hydrophilation agents in dental compounds is found there.

The preparation of the compounds takes place according to customary methods through hydrosilylation of suitable polyethers having an unsaturated group of the formula $Z-(OC_nH_{2n})_x-OT$, where Z is a $C_2$–$C_{18}$ alkenyl group, preferably a $C_2$–$C_{14}$ alkenyl group or a $C_2$–$C_8$, in particular a $C_2$–$C_6$ alkenyl group, with a corresponding Si—H-containing organosilane having the formula Q—H, a catalyst preferably being used which consists of a finely dispersed transition metal or a transition metal compound, preferably based on platinum, palladium or rhodium. It is preferred to separate the catalyst from the carbosilane surfactant after the reaction, in order that the storage stability of a moulding compound into which the carbosilane surfactant is introduced as hydrophilation agent is not threatened. The separation of this catalyst can happen e.g. by adsorption on silica gel, kieselguhr or the like.

For P equal to A—R''', particularly preferred compounds are

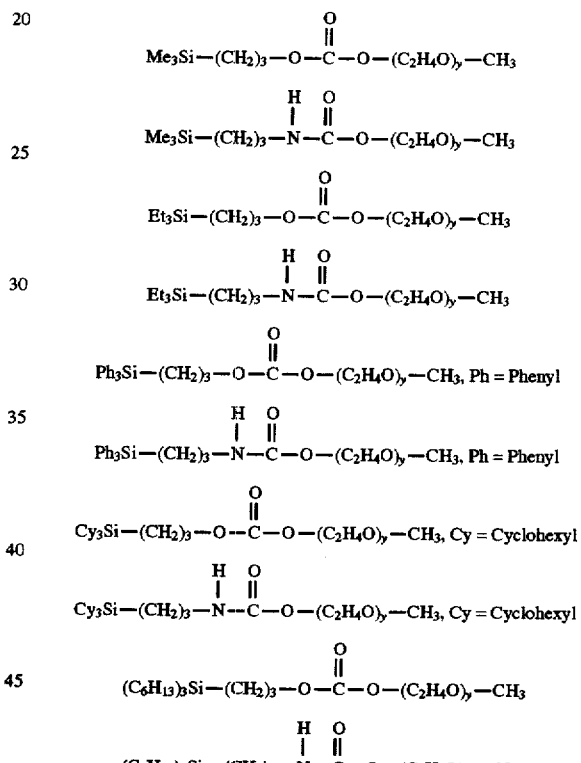

in which y conforms to the relation:

$1 \leq y \leq 20$ or preferably $1 \leq y \leq 10$.

The compounds having the general structure (I) with P=A—R''' are produced essentially analogously to instructions known in the literature. In a first step the production of an unsaturated compound $Z-R'''-(OC_nH_{2n})_x-OT$ takes place, which is transformed by hydrosilylation with a compound Q—H into the product with structure (I) analogously to the manner described above. The introduction of the difunctional groups R''' is described in the following.

For R'''=—NHC(O)— or —OC(O)—: starting from a polyether having the formula $H-(OC_nH_{2n})_x-OT$, a reactive chloroformic acid ester having the formula $Cl-C(O)-(OC_nH_{2n})_x-OT$ is prepared by phosgenation using standard procedures (M. Matzner, R. P. Kurkjy, R. J. Cotter, Chem. Rev. 64 (1964) 645). This can be can be converted in simple reaction with allyl alcohol to a carbonic acid monoallyl mono(polyether) ester (U. Petersen in Houben-Weyl Vol. E4, p. 66) having the formula H$_2$C=CHCH$_2$—O—C(O)—(OC$_n$H$_{2n}$)$_x$—OT or with allyl amine to a N-allyl carbamic acid (polyether) ester (U. Petersen in Houben-Weyl Vol. E4, p. 144) having the formula H$_2$C=CHCH$_2$—NH—C(O)—(OC$_n$H$_{2n}$)$_x$—OT. Suitable in principle is every other unsaturated alcohol ZOH, or every other unsaturated amine having the formula ZNH$_2$, the structure Z—R'''—(OC$_n$H$_{2n}$)$_x$—OT being obtained as product. The obtained alkenyl compounds are reacted with a corresponding Si—H-containing organosilane having the formula Q—H in a manner analogous to the production of structure (I) in a hydrosilylation reaction (I. Ojima in S. Patai, Z. Rappoport "The Chemistry of Organic Silicon Compounds", Wiley 1989), a catalyst being used which consists of finely dispersed transition metal or a transition metal compound, preferably based on platinum, palladium or rhodium. It is preferred to separate the catalyst from the carbosilane surfactant after the reaction (analogously to the production of structure (I) with P not the same as A—R''').

For R'''=—NHC(O)C(O)— or —OC(O)C(O)—: starting from a polyether having the formula H—(OC$_n$H$_{2n}$)$_x$—OT, a reactive chloroglyoxylic acid ester having the formula Cl—C(O)C(O)—(OC$_n$H$_{2n}$)$_x$—OT is prepared by reaction with oxalyl chloride using standard procedures (see e.g. S. J. Rhoads, R. E. Michel, JACS, Vol. 85 (1963) 585). This can be can be converted in simple reaction with allyl alcohol to an oxalic acid monoallyl mono(polyether) ester having the formula HC$_2$=CHCH$_2$—O—C(O)C(O)—(OC$_n$H$_{2n}$)$_x$—OT or with allyl amine to a N-allyl mono(polyether) ester mono-amide having the formula H$_2$C=CHCH$_2$—NH—C(O)C(O)—(OC$_n$H$_{2n}$)$_x$—OT (A. Jackson, Speciality Chemicals 14/5 (1994) 300). Suitable in principle is every other unsaturated alcohol ZOH, or every other unsaturated amine having the formula ZNH$_2$, the structure Z—R'''—(OC$_n$H$_{2n}$)$_x$—OT being obtained as product. The obtained alkenyl compounds are reacted with a corresponding Si—H-containing organosilane having the formula Q—H in a hydrosilylation reaction to give the corresponding carbosilane surfactants. That which was stated above applies as regards catalysis and work-up.

For R'''=—NHC(O) (CH$_2$)$_{n-1}$—, —OC(O) (CH$_2$)$_{n-1}$— or OCH$_2$CH(OH)CH$_2$OC(O) (CH$_2$)$_{n-1}$—: starting from a polyether having the formula H—(OC$_n$H$_{2n}$)$_{x+1}$—OT, an acid-functionalized polyether having the formula HOC(O) (CH$_2$)$_{n-1}$—(OC$_n$H$_{2n}$)$_x$—OT is created by oxidation with nitric acid (H. Henecka in Houben-Weyl Vol. 8, p. 409). The produced acid is transformed for example by means of thionyl chloride into the acid chloride having the formula ClC(O)(CH$_2$)$_{n-1}$—(OC$_n$H$_{2n}$)$_x$—OT (H. Henecka, Houben-Weyl Vol. 8 p. 463, R. Sustmann, H.-G. Korth, Houben-Weyl Vol. E5/1 p. 593) and this is transformed by means of allyl alcohol into the allyl ester having the formula H$_2$C=CHCH$_2$—O—C(O) (CH$_2$)$_{n-1}$—(OC$_n$H$_{2n}$)$_x$—OT (H. Henecka in Houben-Weyl Vol. 8, p. 543) or with allyl amine into the N-allyl amide having the formula H$_2$C=CHCH$_2$—NH—C(O) (CH$_2$)$_{n-1}$—(OC$_n$H$_{2n}$)$_x$—OT (H. Henecka, P. Kurtz in Houben-Weyl Vol. 8, p. 655). Suitable in principle is every other unsaturated alcohol ZOH, or every other unsaturated amine having the formula ZNH$_2$, the structure Z—R'''—(OC$_n$H$_{2n}$)$_x$—OT being obtained as product. The ring-opening reaction of the acid-functionalized polyether having the formula HOC(O) (CH$_2$)$_{n-1}$—(OC$_n$H$_{2n}$)$_x$—OT with allyl glycidyl ether leads to compounds having the formula H$_2$C=CHCH$_2$—OCH$_2$CH(OH)CH$_2$)—OC(O) (CH$_2$)$_{n-1}$—(OC$_n$H$_{2n}$)$_x$—OT (H. Henecka in Houben-Weyl Vol. 8, p. 531).

The obtained alkenyl compounds are reacted with a corresponding Si—H-containing organosilane having the formula Q—H in a hydrosilylation reaction to give the corresponding carbosilane surfactants. That which was stated above applies as regards catalysis and work-up.

For R'''=—OC(O) (CH$_2$)$_y$C(O)—, —NHC(O) (CH$_2$)$_y$C(O)— or —OCH$_2$CH(OH)CH$_2$OC(O) (CH$_2$)$_y$C(O)—: starting from a polyether having the formula H—(OC$_n$H$_{2n}$)$_{x+1}$—OT, a reactive compound having the formula ClC(O) (CH$_2$)$_y$C(O)—(OC$_n$H$_{2n}$)$_x$—OT is obtained by equimolar reaction with a difunctional acid chloride having the formula ClC(O) (CH$_2$)$_y$C(O)Cl using standard procedures. Esters having the formula H$_2$C=CHCH$_2$—O—C(O) (CH$_2$)$_y$C(O)—(OC$_n$H$_{2n}$)$_x$—OT form through subsequent esterification with allyl alcohol (H. Henecka in Houben-Weyl Vol. 8, p. 543); the reaction with allyl amine leads to N-allyl amides having the formula H$_2$C=CHCH$_2$NH—C(O) (CH$_2$)$_y$C(O)—(OC$_n$H$_{2n}$)$_x$—OT (H. Henecka, P. Kurtz in Houben-Weyl Vol. 8, p. 655). Suitable in principle is every other unsaturated alcohol ZOH, or every other unsaturated amine having the formula ZNH$_2$, the structure Z—R'''—(OC$_n$H$_{2n}$)$_x$—OT being obtained as product. The reaction of the free acid (obtainable by hydrolysis of the acid chloride ClC(O) (CH$_2$)$_y$C(O)—(OC$_n$H$_{2n}$)$_x$—OT) with allyl glycidyl ether leads to compounds having the formula H$_2$C=CHCH$_2$—O—CH$_2$CH(OH)CH$_2$OC(O) (CH$_2$)$_y$C(O) —(OC$_n$H$_{2n}$)$_x$—OT (H. Henecka in Houben-Weyl Vol. 8, p. 531). The obtained alkenyl compounds are reacted with a corresponding Si—H-containing organosilane having the formula Q—H in a hydrosilylation reaction to give the corresponding carbosilane surfactants. That which was stated above applies as regards catalysis and work-up.

In the general structural formula (II) given above, R preferably stands for an aliphatic $C_1$-$C_6$ hydrocarbon radical, in particular for a methyl or ethyl radical, for a cycloaliphatic $C_6$-$C_8$ hydrocarbon radical or for an aromatic $C_6$-$C_8$ hydrocarbon radical, in particular for a phenyl radical.

X preferably stands for a $C_2$-$C_{10}$, in particular for a $C_4$-$C_8$ alkylene group, for a $C_6$-$C_{15}$ arylene, in particular p-phenylene, for a cycloaliphatic $C_5$-$C_{10}$, in particular $C_5$-$C_7$ cycloalkylene group or for a polycycloaliphatic $C_8$-$C_{12}$ alkylene group, quite particularly tricyclo (5.2.1.0$^{2,6}$) dec-3(4),8(9)-ylene.

P is preferably a $C_2$-$C_8$, in particular a $C_2$-$C_6$ alkylene group.

T preferably stands for H, for a methyl or ethyl radical or for an acetyl radical.

x preferably stands for a number from 1 to 50 and n preferably has a value of 2 to 2.5.

Particularly preferred polyether carbosilanes are the compounds listed in the following

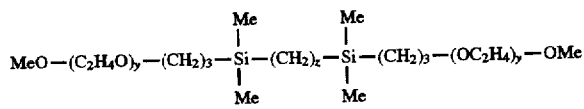

-continued

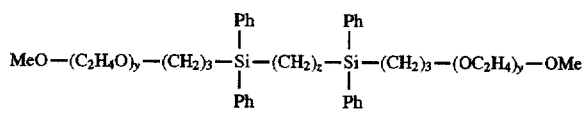

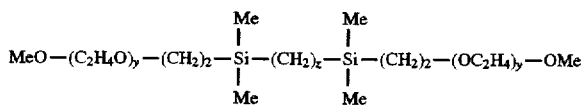

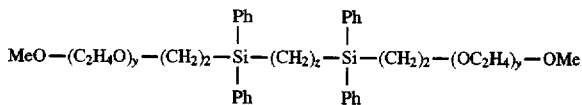

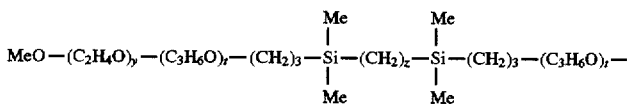

—(OC₂H₄)ᵧ—OMe

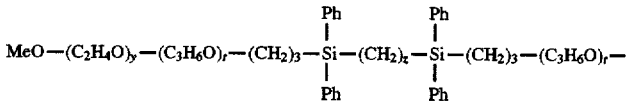

—(OC₂H₄)ᵧ—OMe

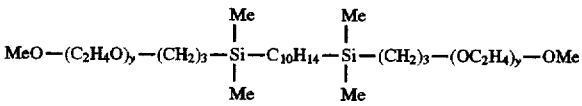

C₁₀H₁₄ = Tricyclo[5.2.1.0²·⁶]dec-3(4), 8(9)-ylene

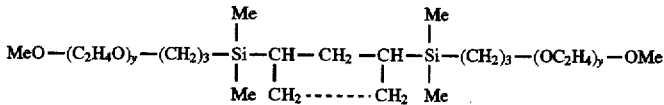

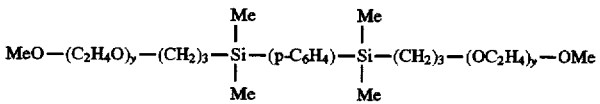

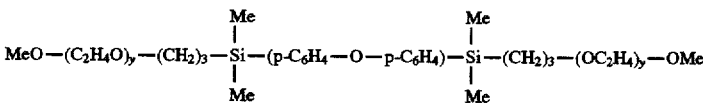

in which y conforms to the relation:

1≦y≦20 or preferably 1≦y≦10, and z conforms to the relation:

2≦z≦8 or preferably 2≦z≦6;

and t conforms to the relation:

0.1·y≦t≦y or preferably 0.15·y≦t≦0.55·y.

The procedure for preparing the compounds having the general structure (II) is that firstly the bis-organosilyl-modified middle piece —SiR₂XSiR₂— is obtained for example by means of coupling reaction from a chlorine-functionalized silane HSiR₂Cl and a di-Grignard compound ClMgXMgCl (K. Nützel in Houben-Weyl, Vol. 13/2a p. 101, S. Pawlenko in Houben-Weyl Vol. 13/5 p. 85) or by bis-hydrosilylation of an alkadiene with an organo-H silane e.g.

R₂SiHCl (I. Ojima in S. Patai, Z. Rappoport "The Chemistry of Organic Silicon Compounds", Wiley 1989 or S. Pawlenko in Houben-Weyl Vol. 13/5 p. 85). This radical Q'=— SiR₂XSiR₂— is either already Si—H-terminated, or is subsequently functionalized for the further reaction by hydrogenation of Si—Cl groups with LiAlH₄ to give compounds having the formula H—SiR₂XSiR₂—H. This compound is joined with unsaturated polyether radicals having the formula Z—(OCₙH₂ₙ)ₓ—OT, Z being as defined above, in a hydrosilylation reaction (analogous to the production and work-up of structure (I)).

If P is the same as A—R''', the introduction of this group takes place analogously to the processes described in the case of structure (I).

In the general structural formula (III) given above, R preferably stands for an aliphatic C₁-C₆ hydrocarbon radical, in particular a methyl or ethyl radical, for a cycloaliphatic C₆-C₈ hydrocarbon radical or for an aromatic C₆-C₈ hydrocarbon radical, in particular a phenyl radical.

R' preferably stands for a $C_1$–$C_6$ alkylene radical and in particular for a methylene or ethylene radical.

P is preferably a $C_2$–$C_8$, in particular a $C_2$–$C_6$ alkylene group.

a is preferably 0, x preferably stands for a number from 1 to 50 and n preferably has a value of 2 to 2.5.

Particularly preferred polyether carbosilanes are the compounds listed in the following

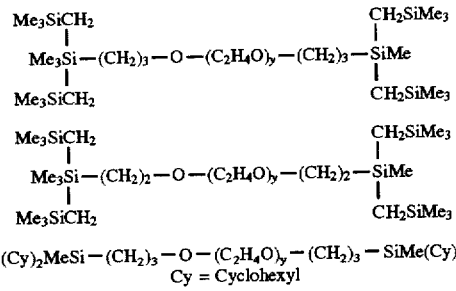

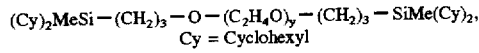

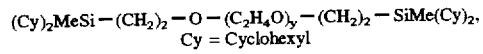

in which y conforms to the relation:

$1 \leq y \leq 30$ or preferably $2 \leq y \leq 20$.

The compounds having the general structure (III) are joined, starting from unsaturated polyethers having the formula Z—$(OC_nH_{2n})_x$—O—Z, Z being as defined above, in a hydrosilylation reaction with Si—H-containing organosilanes having the form Q—H (analogous to the production and treatment of structure (I). The production of the linear unsaturated compounds Z—$(OC_nH_{2n})_x$—O—Z is described for example in DE-A 37 41 575.

If P is the same as A—R''', the introduction of this group takes place analogously to the processes described in the case of structure (I).

In the general structural formula (IV) given above, Q preferably stands for $R_3Si$—. R preferably stands for an aliphatic $C_1$–$C_6$ hydrocarbon radical, in particular a methyl or ethyl radical, for a cycloaliphatic $C_6$–$C_8$ hydrocarbon radical or for an aromatic $C_6$–$C_8$ hydrocarbon radical, in particular a phenyl radical.

P' is preferably either a 2,2-bis-alkylene-acetyl group (—$((CH_2)_k)_2CHC(O)$—) with $C_1$–$C_5$ (k=1–5), in particular $C_1$–$C_3$ alkylene groups (k=1–3), a 2-alkylene-2-alkyl-acetyl group (—$((CH_2)_k)CHRC(O)$—) with a $C_1$–$C_5$ (k=1–5), in particular with a $C_1$–$C_3$ alkylene (k=1–3) and with an alkyl group R=$C_2$–$C_{14}$ or a 2-alkylene-acetyl group (—$((CH_2)_k)_2CHC(O)$—) with a $C_1$–$C_5$ (k=1–5), in particular with a $C_1$–$C_3$ alkylene group (k=1–3).

T preferably stands for H, for a methyl or ethyl radical or for an acetyl radical.

x preferably stands for a number from 1 to 50 and n preferably has a value of 2 to 2.5.

Particularly preferred polyether carbosilanes are the compounds listed in the following

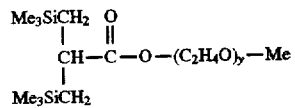

-continued

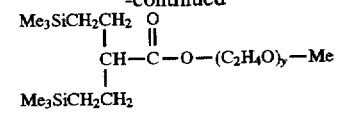

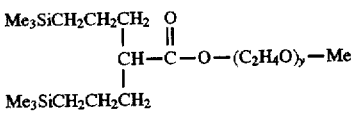

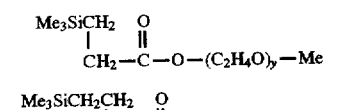

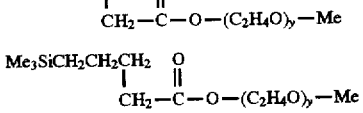

in which y conforms to the relation:

$1 \leq y \leq 20$ or preferably $1 \leq y \leq 10$.

The compounds of the general structure (IV) are produced starting from malonic acid dialkyl ester by deprotonation of this ester with strong bases and alkylation of the resultant carbanion with compounds having the formula Q—$(CH_2)_k$ Cl or R—Cl. In the case of the twice-alkylated compounds with P'=(—$(CH_2)_k)_2CHC(O)$— or —$(CH_2)_kCHRC(O)$—, this procedure is carried out twice. The resultant alkylated malonic ester derivatives are alkalinely saponified and thermally decarboxylated or simultaneously saponified and decarboxylated in the acid medium (S. Pawlenko in Houben-Weyl Vol. 13/5, 1980, p. 21, 75; L. H. Sommer, J. R. Gold, M. Goldberg, M. S. Marans, 71 (1949) 1507, H. Henecka in Houben-Weyl Vol. 8 p. 600). The resultant free monocarboxylic acids having the form QP'—OH are esterified by means of entrainment esterification with a polyether having the formula H—$(OC_nH_{2n})_x$OT (H. Henecka in Houben-Weyl Vol. 8 p. 522).

An alternative way is the preparation of alkylated malonic esters of the formula $Z_{2-j}R_jC(COOR)_2$ with j=0 or 1 by alkylation of malonic acid dialkyl ester with RCl and ZCl (e.g. allyl chloride) under the influence of a strong base. After saponification and decarboxylation, this substituted carboxylic acid can be esterified with the above-mentioned polyether having the formula H$(OC_nH_{2n})_x$OT (H. Henecka in Houben-Weyl Vol. 8 p. 522). The resultant product is now coupled with a Si—H-containing organosilane Q—H by hydrosilylation (analogous to the production and work-up of structure (I)) to give carbosilane surfactants having the structure (V).

In the general structural formula (V) given above, Q" stands for an oligomeric or polymeric carbosilane, in which preferably 20–70% of the silicon atoms are substituted by a radical —(P—$(OC_nH_{2n})_x$OT). Otherwise the Si atoms preferably bear methyl, ethyl or phenyl radicals. The carbosilane chain preferably consists, alongside the silicon atoms, of L groups, L preferably being an alkylene radical $C_1$–$C_3$ or a p-phenylene radical. The chain bears methyl, ethyl, propyl or phenyl groups as end groups.

P is preferably a $C_2$–$C_8$, in particular a $C_2$–$C_6$ alkylene group.

T preferably stands for H, for a methyl or ethyl radical or for an acetyl radical.

x stands for a number from 1 to 200, preferably a number from 1 to 50, and n is an average number from 1 to 6, preferably a value of 2 to 2.5.

Particularly preferred polyether carbosilanes are the compounds listed in the following

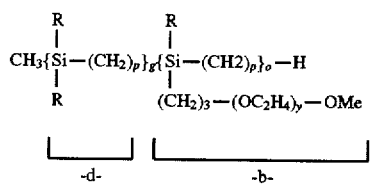

in which y conforms to the relation:

1≦y≦20 or preferably 1≦y≦10;

and p can equal 2 or 3;

let o preferably be 3–1000 and g in particular conforms to the relation:

4-o≧g≧0.42-o.

R is in this case preferably methyl, ethyl or phenyl.

The carbosilane chain can consist of alternating, statistical or block copolymer units.

A synthesis route to such carbosilane surfactants is the reaction of organohydrogen silanes having 2 SiH groups with an organosilane having two unsaturated groups in a hydrosilylation reaction, where at least one of the said organosilanes must bear a group which can be transformed into a Si—H unit—for example a halogen group which can be reduced by hydrogenation for example with lithium alanate—and which does not negatively influence the hydrosilylation reaction. Examples of the difunctional organohydrogen silanes are diphenyl silane or phenyl methyl silane, methyl bromosilane or phenyl chlorosilane. Examples of the unsaturated silanes are divinyl dimethyl silane, diallyl dimethyl silane, divinyl diphenyl silane, diallyl diphenyl silane, divinyl methyl chlorosilane or divinyl methyl bromosilane, diallyl methyl chlorosilane or diallyl methyl bromosilane. The hydrosilylation product is a polymeric substance whose molecular weight can be set by adding monofunctional unsaturated silanes—e.g. vinyl trimethyl silane—or Si—H compounds—e.g. triphenyl silane or triethyl silane (S. Pawlenko in Houben-Weyl Vol. 13/5 p. 328).

After subsequent hydrogenation of the Si halogen group to give the Si—H group with $LiAlH_4$, hydrosilylation is carried out with an unsaturated polyether having the formula $Z-(OC_nH_{2n})_x-OT$, Z being defined as above, under platinum catalysis (analogous to the production of structure (I)) to give the carbosilane surfactant.

Another possibility for preparing a carbosilane surfactant having the general structure (V) comprises the production by known methods of silacyclobutanes having the formula $(CH_2)_3SiHR$ (N. S. Nametkine, V. M. Vdovine, J. Polym. Sci C (1963) 1043, R. Damrauer, Organometal. Chem. Rev. A, 8 (1972) 67).

These silacyclobutanes can be hydrosilylated with unsaturated polyethers having the formula $Z-(OC_nH_{2n})_x-OT$, Z being defined as above, under platinum catalysis, for example according to processes described in the above literature, and then—optionally with the addition of silacyclobutanes without polyether radicals—polymerized in ring-opening manner to give carbosilane surfactants having the general formula (V).

The silacyclobutanes having the formula $(CH_2)_3SiR-P-(OC_nH_{2n})_x-OT$ that have formed upon this hydrosilylation can for example be thermally polymerized, e.g. analogously to the processes described in U.S. Pat. No. 3,046,291. The polymerization can also take place in the presence of a transition metal catalyst, preferably based on platinum (see e.g. D. R. Weyenberg, L. E. Nelson, Journal of Organic Chemistry, 30 (1965) 2618 or U.S. Pat. No. 3,445,495). Also conceivable is an acceleration of the polymerization by anionic compounds, such as KOH or lithium alkyls (e.g. C. X. Liao, W. P. Weber, Polymer Bulletin 28 (1992) 281. The polymerization can take place with or without solvent.

Another way comprises the polymerization of the SiH-bearing silacyclobutanes by known methods accompanied by ring-opening and the subsequent hydrosilylation of the SiH-containing polycarbosilanes with polyethers having the formula $Z-(OC_nH_{2n})_x-OT$, Z being defined as above (C. X. Liao, W. P. Weber, Macromol. 26(4) (1993) 563).

In principle, SiH-containing poly- or oligocarbosilanes can also be produced by reaction of di-Grignard compounds with $Cl_2SiMeH$ using $ClSiMe_3$ or $ClSiMe_2H$ as chain breaker. There then occurs analogously to above the hydrosilylation of the products with the unsaturated polyethers.

With all the described production processes by hydrosilylation, the platinum catalyst is preferably removed after the production by already described processes.

The following examples serve to explain the invention. The invention is not limited to the examples.

EXAMPLES

The measurement of the edge angle takes place with a G1/G40 (Krüiss) contact angle measurement system. The G1 edge angle measurement apparatus makes possible the precise reproduction of drop profiles on surfaces of solids. The G40 measurement system comprises a video tube with beam splitter, so that simultaneous observation of a drop through the goniometer eyepiece (drop size) and the video camera (digital image evaluation) is made possible.

The measurement takes place on the lying drop at 23° C. and 50% relative atmospheric humidity. 30 minutes after the start of mixing of the compounds a drop, always of the same size, of a calcium sulphate dihydrate solution saturated at 23° C. is deposited on the elastomer that has hardened to a smooth surface between glass plates, and measurement begins at once. The 10-second value is used for the evaluation.

In the examples, the HLB value in question of the hydrophilation agents is given. The HLB value is a measure of the water- and grease-friendliness of compounds (see Ullmann's Encyclopedia of Industrial Chemistry, Vol. A25, page 784 et seq. (1994)). The HLB value of the hydrophilation agents according to the invention should lie between roughly 5 and 15 as a rule.

Production example 1

9.0 g of a monomethyl monoallyl-terminated polyethylene glycol having an average molecular weight of 450 are added to a solution of 4.7 g triethyl silane in 28 ml toluene. A platinum catalyst is added and the reaction mixture is stirred at 100° C. until there are no more allyl groups present according to the $^1$H-NMR spectrum of the untreated product. After filtration over silica gel and removal of the volatile constituents under vacuum, 4.0 g of a compound 1 are obtained whose NMR spectrum is consistent with the following structural formula (n=ca. 7–10):

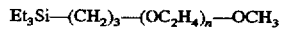

The HLB value is ca. 14.

Application example 1

28.2 parts of a vinyl end-stopped polydimethyl siloxane having a viscosity of 2000 mPa.s at 23° C., 2.5 parts of a SiH group-containing polydimethyl siloxane having a viscosity of 60 mPa.s at 23° C., 9.7 parts of a polydimethyl siloxane having a viscosity of 50 mPa.s at 23° C., 8.1 parts of a silanized pyrogenic silicic acid, 49.1 parts finest quartz powder, 0.3 parts inorganic colour pigment and 2.3 parts of the hydrophilation agent from production example 1 are combined in a kneader by mixing to give a homogeneous base paste.

The catalyst paste is produced by mixing 20.6 parts of a vinyl end-stopped polydimethyl siloxane having a viscosity of 2000 mPa.s at 23° C., 7.5 parts of a silanized pyrogenic silicic acid, 53.1 parts finest quartz powder, 13.3 parts of a polydimethyl siloxane having a viscosity of 50 mPa.s at 23° C., 3.4 parts of a solution of 1.3 parts of a complex comprising platinum and divinyl tetramethyl disiloxane in a polydimethyl siloxane having a viscosity of 50 mPa.s at 23° C. and 2.3 parts of the hydrophilation agent from production example 1.

Measurement of the wetting edge angle 50 g base paste and 10 g catalyst paste are fully mixed. After some minutes, a rubber-elastic compound is obtained. 30 minutes after production, the edge angle is measured as 42°. The test-pieces are then disinfected for 10 minutes in the disinfection immersion bath customary in the trade (Impresept, ESPE). The testpieces are removed, briefly rinsed under running cold water and left to dry for 2 hours in air of 23° C. and 50% relative humidity. The edge angle is then measured again as 54°.

For comparison, corresponding compounds are hydrophilated with two polyether siloxane surfactants customary in the trade, "Silwet" L-77 and "Tegopren" 5878. Under identical conditions, the edge angle is measured before and after disinfection. The result is summarized in the following table.

A commercially available hydrophilated silicone dental impression compound "Reprosil" (a compound according to EP-B-0 231 420) was also examined for comparison purposes. The result is likewise given in the following table.

In the case of another disinfection treatment such as regularly takes place in practice, the differences in the relative edge angle increases between the compounds according to the invention and the known compounds become even greater.

Industrial application test 50 g of base paste and 10 g of catalyst paste are fully mixed with each other within 30 seconds. A dimension testpiece according to ADA 19 is moulded with the admixed compound. After some minutes, a rubber-elastic moulding of the testpiece is obtained. This moulding is cast 30 minutes after the start of mixing with an aqueous plaster suspension (100 g Geostone/23 g water). The model obtained after the plaster sets has a satisfactory surface.

Dimensional stability

The dimensional stability is measured as −0.1% according to ADA 19.

Measurement of storage stability

Base paste and catalyst paste are stored separate from each other over a period of 14 days at 70° C. After this time both pastes are cooled to 23° C. 50 g of base paste and 10 g of catalyst paste from this ageing test are fully mixed with each other. The setting pattern is measured on a cyclovis-cograph. The setting pattern does not differ from that of the freshly produced, non-aged pastes.

TABLE

| Example | Hydrophilation agent | EA before disinf. | EA after disinf. | Relative EA increase |
|---|---|---|---|---|
| 2 | as per production example | 42° | 54° | 28% |
| Comp. 1 | Silwet L-77 | 45° | 72° | 60% |
| Comp. 2 | Tegopren 5878 | 47° | 74° | 57% |
| Reprosil | as per EP-B-0 231 420 | 45° | 65° | 44% |

Production example 2

Analogously to the production instructions in EP-A-0 367 381 (Example 1, page 4), bis(trimethyl silyl methyl) methyl silane was produced. This was reacted analogously to Example 1 in GB-A 1 520 421 with a methyl allyl-terminated polyethylene glycol having an average molecular weight of 350 in a hydrosilylation reaction. After work-up analogous to production example 1, a compound 2 was obtained whose NMR spectrum is consistent with the following structural formula (n=ca. 5–8):

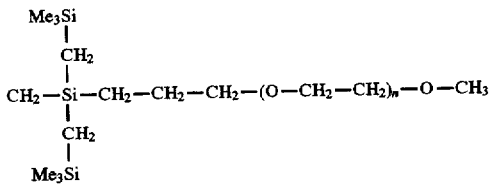

The HLB value of the material is ca. 11.

In the case of the production of bis(trimethyl silyl methyl) methyl silane, a disilane having the following structure forms as by-product:

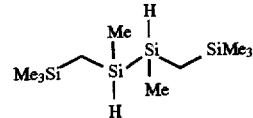

The substance is preferably separated upon work-up e.g. by distillation. However, if the substance forms in only small proportions, it can also be left in the production process and produces the following structure upon hydrosilylation:

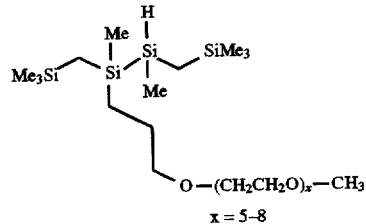

This is likewise a carbosilane surfactant having a hydrophilating effect. The possibility of producing carbosilane surfactants with disilane structure is not limited to this example.

Application example 2

Analogously to application example 1, a base and catalyst paste is kneaded, only 1 part each of the hydrophilation agent from production example 2 being introduced both into the catalyst and also the base paste. The 10-second edge angle, which is measured analogously to application example 1, is 35(±3)°. The testpieces are then disinfected for an hour in the disinfection immersion bath customary in the trade (Impresept, ESPE). The testpieces are removed, briefly rinsed under running cold water and left to dry for 2 hours in air of 23° C. and 50% relative humidity. The edge angle is then measured anew. 10-second edge angle is again 35(±3)°.

In the case of the industrial application examination analogous to application example 1, a plaster model having a bubble-free, satisfactory surface is obtained after the casting of a moulding with plaster suspension. The dimensional stability according to ADA 19 is measured as −0.2%. The storage stability is examined analogously to application example 1, and after 14 days' storage at 70° C. there is no change in the setting pattern of stored compared with non-aged pastes.

Production example 3

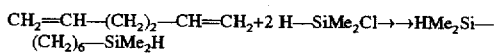

82.1 g (1.0M) 1,6-hexadiene are reacted in 100 ml aromatic solvent with Pt catalyst and hydrosilylated at 70° C. with 208.2 g (2.20M) dimethyl chlorosilane. The reaction mixture is columned over $Al_2O_3$, concentrated to half the volume and hydrogenated with 18.5 g (0.5M) $LiAlH_4$ solution in THF. After hydrolytic work-up, the solvent is distilled off from the organic phase. A clear colourless oil remains behind. Yield of the above silane: 145.8 g—72%.

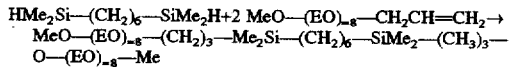

30 g (0.15M) of the obtained silane are reacted in 50 ml toluene with 86.5 g (0.22M) polyethylene glycol methyl allyl ether and hydrosilylated by means of platinum catalyst. The product is purified by means of an $Al_2O_3$ column and freed of solvent. Yield of obtained polyether carbosilane: 98 g—90%.

Production example 4

Polyethylene glycol ($M_W$=400 g/mol) is allylated as per instructions (M. Galin, A. Mathis, Macromol. 15 (1981) 677).

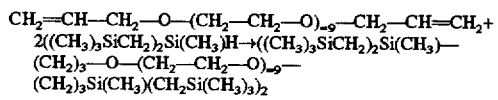

30 g (0.063M) of the obtained PEG-400 diallyl ether are hydrosilylated with 32.7 g (0.15M) bis(trimethyl silyl methyl) methyl silane in an aromatic solvent under platinum catalysis. The reaction lasts 80 hours at 100° C. Yield of obtained polyether carbosilane: 47 g—81%.

We claim:

1. A dental impression compound on the basis of addition-crosslinking silicones, condensation-crosslinking silicones, polyether silicones or polyethers, containing 0.1 to 10 wt.-%, relative to the total weight of the compound, of a polyether carbosilane as hydrophilation agent, the polyether carbosilane having the general formulae:

$$Q-P-(OC_nH_{2n})_x-OT \quad (I)$$

in which:

Q stands for $R_3Si-$ or

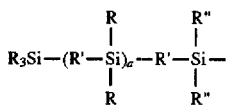

where every R in the molecule can be the same or different and stands for an aliphatic $C_1-C_{18}$, a cycloaliphatic $C_6-C_{12}$ or an aromatic $C_6-C_{12}$ hydrocarbon radical, which can optionally be substituted by halogen atoms.

R' is a $C_1-C_{14}$ alkylene group,

R" is R in the case of a≠0 or is R or $R_3SiR'$ in the case of a=0, and a=0–2;

P stands for a $C_2-C_{18}$ alkylene group, or A—R'", where A represents a $C_2-C_{18}$ alkylene group and R'" a functional group from the following list:

—NHC(O)—, —NHC(O) $(CH_2)_{n-1}$—, —NHC(O)C(O)—,

—NHC(O) $(CH_2)_vC(O)$—, —OC(O)—,

—OC(O) $(CH_2)_{n-1}$—, —OC(O)C(O)—, —OC(O) $(CH_2)_v C(O)$—,

—OCH$_2$CH(OH)CH$_2$OC(O) $(CH_2)_{n-1}$—,

—OCH$_2$CH(OH)CH$_2$OC(O) $(CH_2)_vC(O)$— with v=1–12;

T is H, a $C_1-C_4$ alkyl radical or a $C_1-C_4$ acyl radical;

x is a number from 1 to 200; and n is an average number from 1 to 6;

$$Q'-(P-(OC_nH_{2n})_x-OT)_2 \quad (II)$$

in which:

Q' is $-SiR_2-X-SiR_2-$;

X is a divalent hydrocarbon radical, a $C_1-C_{18}$ alkylene, a $C_6-C_{20}$ arylene, a $C_5-C_{15}$ cycloalkylene or a $C_5-C_{15}$ polycycloalkylene radical, which radical can optionally bear oxygen-containing groups, and where all other symbols have the above meaning;

$$Q-P-(OC_nH_{2n})_x-OP-Q \quad (III)$$

in which all symbols have the above meaning; or $$Q"(-P-(OC_nH_{2n})_xOT)_{o'} \quad (V)$$

in which:

Q" stands for an oligomeric or polymeric carbosilane, where at least one silicon atom, are substituted by the radical (—P—$(OC_nH_{2n})_x$OT) and thus o' is ≧1; and where all other symbols have the above meaning.

2. The dental impression compound according to claim 1, wherein the polyether carbosilane is selected from the group consisting of:

$$Et_3Si-(CH_2)_3-O-(C_2H_4O)_y-CH_3$$

$$Et_3Si-CH_2-CH_2-O-(C_2H_4O)_y-CH_3$$

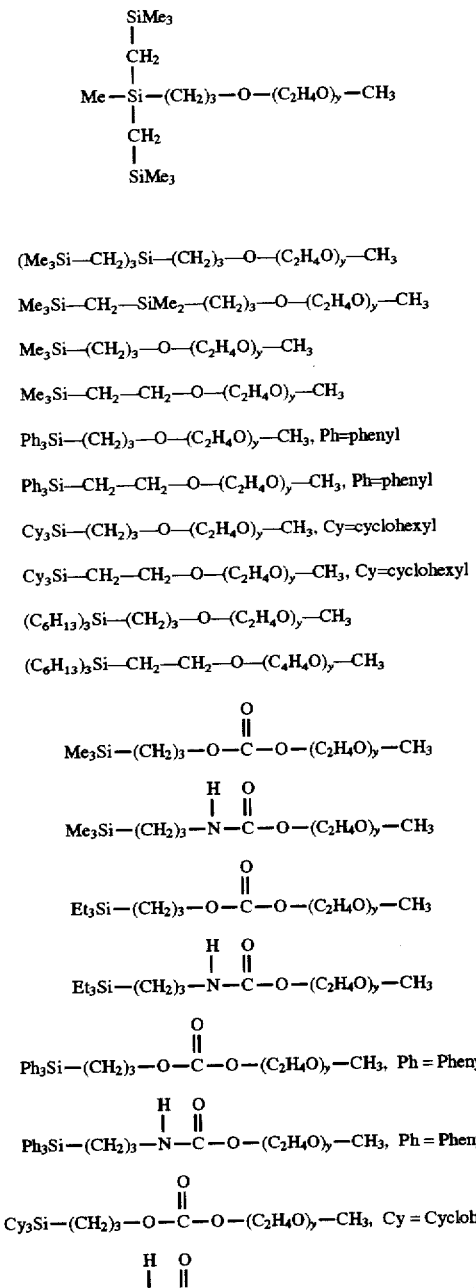

in which y conforms to the relation:

$1 \leq y \leq 20$.

3. The dental impression compound according to claim 1, wherein the polyether carbosilane is selected from the group consisting of:

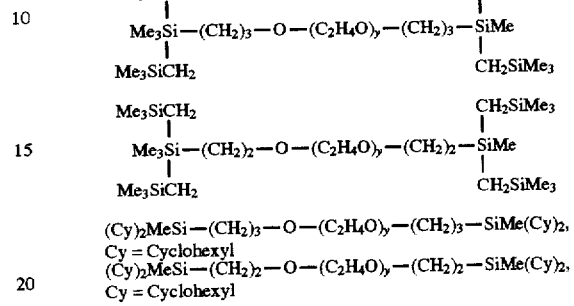

(Cy)$_2$MeSi—(CH$_2$)$_3$—O—(C$_2$H$_4$O)$_y$—(CH$_2$)$_3$—SiMe(Cy)$_2$,
Cy = Cyclohexyl
(Cy)$_2$MeSi—(CH$_2$)$_2$—O—(C$_2$H$_4$O)$_y$—(CH$_2$)$_2$—SiMe(Cy)$_2$,
Cy = Cyclohexyl in which y conforms to the relation:

$1 \leq y \leq 30$.

4. In a process for the production of dental mouldings, the improvement comprising the step of providing a dental impression compound hydrophilated with a polyether carbosilane;

wherein the basis of the dental impression compound is formed from addition- or condensation-crosslinking silicones, polyether silicones or polyethers, and wherein the polyether carbosilane is not hydrolysable.

5. The dental impression compound according to claim 1, wherein the polyether carbosilane is selected from the following compounds:

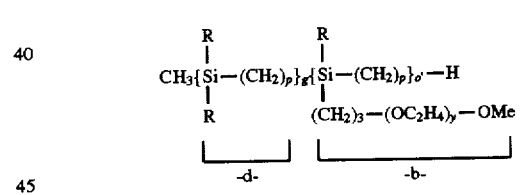

in which y conforms to the relation:

$1 \leq y \leq 20$;

and p equals 2 or 3;

o' is 3–1000 and g conforms to the relation:

$4 \cdot o' \geq g \geq 0.42 \cdot o'$, and

R is methyl, ethyl or phenyl.

6. The dental impression compound according to claim 1, wherein the polyether carbosilane is selected from the following compounds:

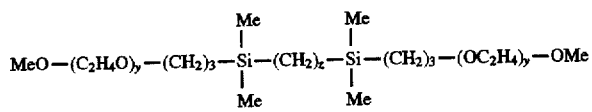

-continued

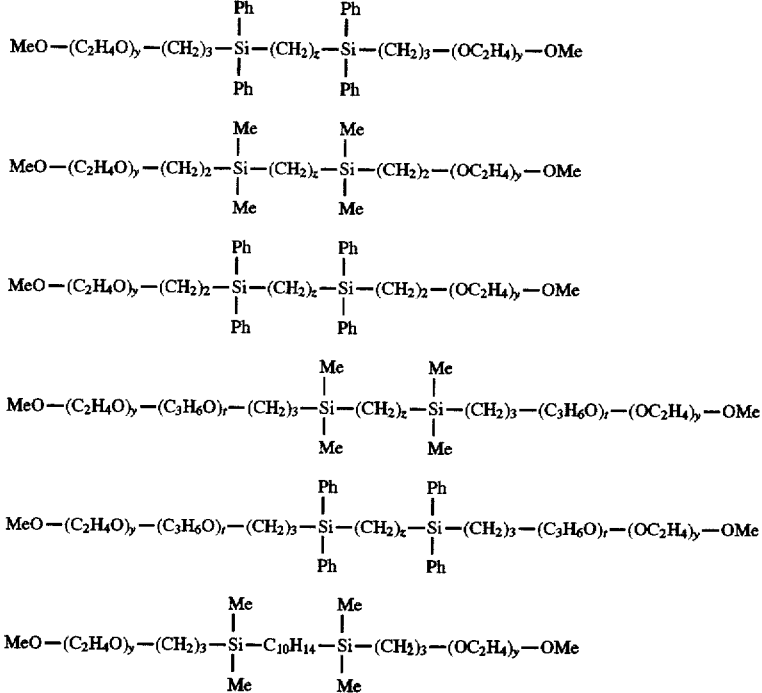

$C_{10}H_{14}$ = Tricyclo(5.2.1.0$^{2,6}$)dec-3(4), 8(9)-ylene

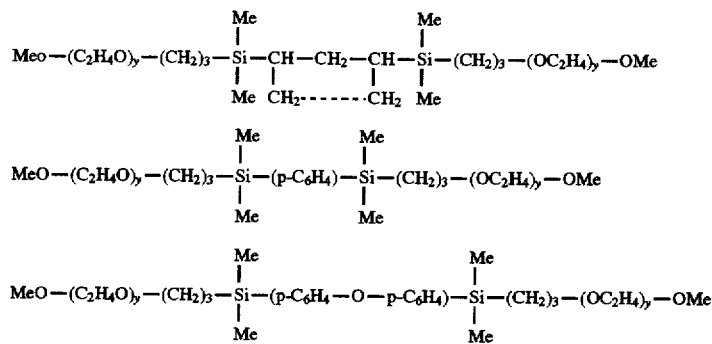

in which y conforms to the relation:

$1 \leq y \leq 20$, and z conforms to the relation:

$2 \leq z \leq 8$;

and t conforms to the relation:

$0.1 \cdot y \leq t \leq y$.

7. The dental impression compound of claim 1, wherein P is a $C_2$–$C_{14}$ alkylene group.

8. The dental impression compound of claim 1, wherein 20–70% of the silicon atoms of Q" are substituted by the radical (—P—(OC$_n$H$_{2n}$)$_x$OT).

* * * * *